United States Patent [19]
Postlethwaite

[11] Patent Number: 5,519,754
[45] Date of Patent: May 21, 1996

[54] VIDEOFLUOROSCOPY DEVICE

[76] Inventor: John R. Postlethwaite, 2700 Bayshore Blvd., B-11-110, Dunedin, Fla. 34698

[21] Appl. No.: 179,368

[22] Filed: Jan. 10, 1994

[51] Int. Cl.$^6$ ..................................................... H05G 1/02
[52] U.S. Cl. ......................................... 378/197; 378/190
[58] Field of Search .............................. 378/190, 195–197

[56] References Cited

U.S. PATENT DOCUMENTS

| | | | |
|---|---|---|---|
| 3,281,598 | 10/1966 | Hollstein | 378/196 |
| 4,178,513 | 12/1979 | Dubois et al. | 250/491 |
| 4,926,453 | 5/1990 | Toniolo | 378/197 |

OTHER PUBLICATIONS

Brochure titled "Joint Motion Imager from Concord" *applicant became aware of brochure in Dec. 1992.

*Primary Examiner*—Craig E. Church
*Attorney, Agent, or Firm*—James E. Larson; Herbert W. Larson

[57] ABSTRACT

A videofluoroscopy device having a vertical housing and a c-arm supporting an x-ray device is provided. The vertical housing encloses a first channel wherein a center screw is mounted. The center screw engages a mounting block having a threaded aperture formed therein, the mounting block being attached to the c-arm. A motor engaging the center screw turns the center screw in reversible directions thereby causing the center screw to communicate with the c-arm and moving the c-arm along a longitudinal axis to record a real time video x-ray image of a patient. A video monitor and video tape recorder are connected to the x-ray device by a video cable.

19 Claims, 5 Drawing Sheets

VIDEOFLUOROSCOPY DEVICE

BACKGROUND OF THE INVENTION

1. Field of the Invention

This invention relates to a videofluoroscopy device. More particularly, it relates to an improvement in the c-arm movement mechanism of the videofluoroscopy device.

2. Description of Prior Art

Videofluoroscopy devices are known in the prior art and are most commonly used by doctors and practitioners in the fields of chiropractic, orthopedic, osteopathic, and sports medicine. The videofluoroscopy device allows a doctor or practitioner to assess problems or abnormalities of a patient's joints, muscles, or bones by recording a real time x-ray image of such joints, muscles, and bones on video tape. The video tape can be reviewed at the doctor or practitioner's leisure, allowing for careful and precise evaluation of a particular problem which might not be evident from an external exam or from conventional x-ray photos.

Most videofluoroscopy devices are relatively small in design and mount to a wall. The device may be used in an office setting or in a mobile medical vehicle. The videofluoroscopy device mainly consists of a vertical housing enclosing a movement mechanism, the movement mechanism operating a c-arm, the c-arm mounted perpendicularly to a longitudinal axis of the vertical housing and supporting an x-ray device.

The movement mechanism directs the c-arm upward and downward along the longitudinal axis of the vertical housing. The x-ray device supported upon the c-arm transmits a real time x-ray image to a video tape recorder thereby recording the movement of the entire body of a patient. In particular, the device records x-ray images of the joints, muscles, and bones and their corresponding movements.

The prior art discloses a pulley system for moving the c-arm. The pulley system is not reliable and has caused the c-arm to be unstable during use. The unstable c-arm renders undesirable results in the video recording process. The recorded video tape image may be blurred and could contain excessive motion. Such poor results renders a video tape unusable, thereby wasting a doctor's money and time, as well as requiring the patient to be video taped again in front of the videofluoroscopy device. These poor results are even more evident when the videofluoroscopy device is used in a mobile medical vehicle.

Additional problems with the prior art device include too many working parts in the movement mechanism thereby necessitating precise tuning and alignment of the parts to yield a desirable result, as well as causing excessive costs when repair is needed. Still further problems involve the pulley system cables becoming disengaged from the pulley wheels causing the videofluoroscopy device to not function and requiring dismantling the device to reset the cables on the wheels.

There is a need to improve the movement mechanism in the prior art videofluoroscopy device to correct the problems currently being experienced.

SUMMARY OF THE INVENTION

I have invented an improvement to the movement mechanism of a videofluoroscopy device which will yield better video taped results of a real time x-ray image to a doctor or practitioner. The superior results of my device will eliminate repeated taping of a patient in front of the x-ray generator to render a usable tape. My device includes less movable parts which reduces manufacture and repair costs.

My videofluoroscopy device has a vertical housing enclosing a center worm screw within a first channel, the screw communicating with a c-arm supporting an x-ray device. A motor mounted at a bottom end of the vertical housing engages and operates the worm screw. A screw engagement element having a threaded aperture secured to a mounting block engages the worm screw through the threaded aperture. The mounting block is secured to a back side of the c-arm. A switch activates the motor to allow the c-arm to move in either direction along the longitudinal axis of the vertical housing. Limiting switches mounted at top and bottom ends of the vertical housing prevent the c-arm from reaching an upper or lower limit which would cause the c-arm to disengage from the worm screw. A pair of guide rails mounted in the first channel of the vertical housing, paralleling the worm screw on opposed sides, assist the c-arm in its movement along the longitudinal axis of the vertical housing by engaging a pair of stabilizing elements. The stabilizing elements are secured to the mounting block with intermediate spacing members between the mounting block and the stabilizing elements. The stabilizing elements enclose a set of bearings to facilitate the communication between the stabilizing elements and the guide rails.

BRIEF DESCRIPTION OF THE DRAWINGS

The invention may be best understood by those having ordinary skill in the art by reference to the following detailed description when considered in conjunction with the accompanying drawings in which.

DETAILED DESCRIPTION OF THE INVENTION

Throughout the following detailed description, the same reference numerals refer to the same elements in all figures.

Figure 1:
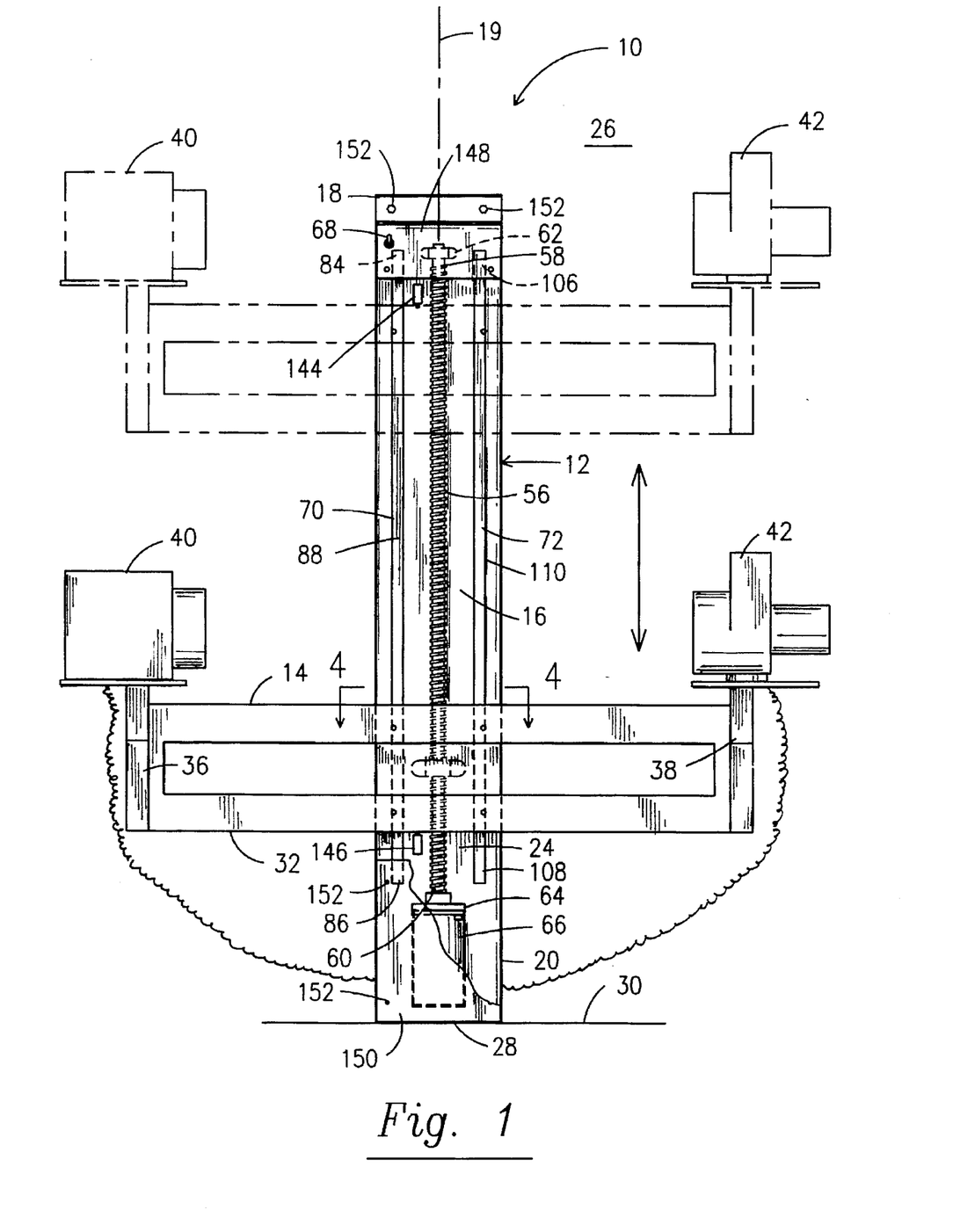
FIG. 1 is a front elevational view of a videofluoroscopy device of this invention.
Figures 2, 3:
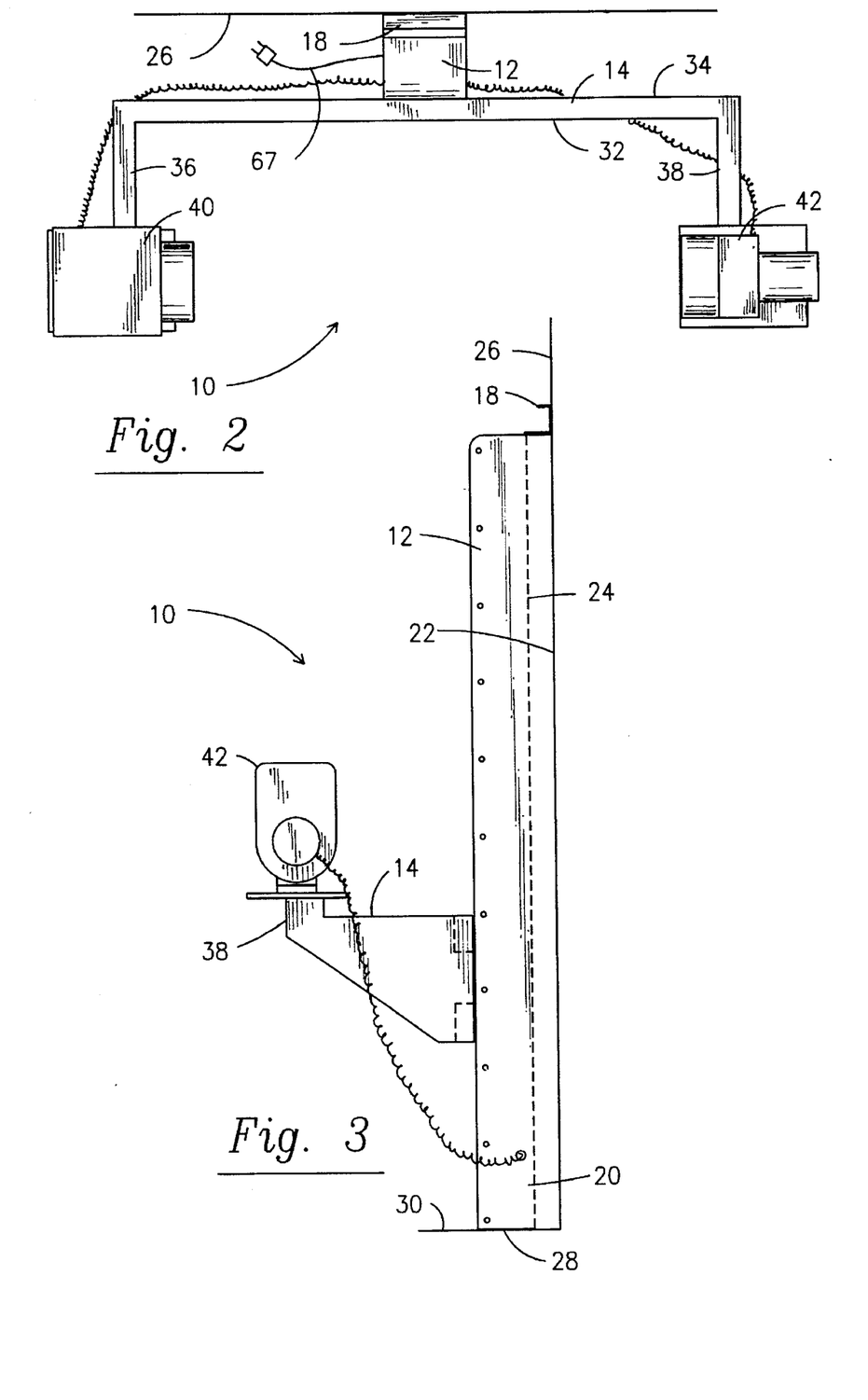
FIG. 2 is a top plan view of the device.
FIG. 3 is a right side elevational view of the device.

Referring to FIG. 1, a videofluoroscopy device 10 has a vertical housing 12 and a c-arm 14. Vertical housing 12 encloses a first channel 16 and has a top and bottom end, 18 and 20 respectively. A longitudinal axis 19 runs from top end 18 to bottom end 20 of vertical housing 12. Vertical housing 12 further includes a back wall 22 spaced from an intermediate wall 24, as shown in FIG. 3. Back wall 22 is placed against a supporting wall 26 of either a building or mobile vehicle. A bottom surface 28 of vertical housing 12 rests upon a floor 30 of either a building or mobile vehicle, such that vertical housing 12 and longitudinal axis 19 are perpendicular to floor 30. Vertical housing 12 is secured to supporting wall 26, preferably by bolts.

C-arm 14 has opposed front and back surfaces, 32 and 34 respectively, and opposed first and second ends, 36 and 38 respectively, as shown in FIG. 2. FIG. 1 shows first end 36 supporting an x-ray generator 40 and second end 38 supporting an x-ray image intensifier 42, although x-ray generator 40 and x-ray image intensifier 42 are interchangeable upon first end 36 and second end 38 of c-arm 14 and are placed at first and second ends, 36 and 38 respectively, in accordance with a user's preference.

Figure 4:
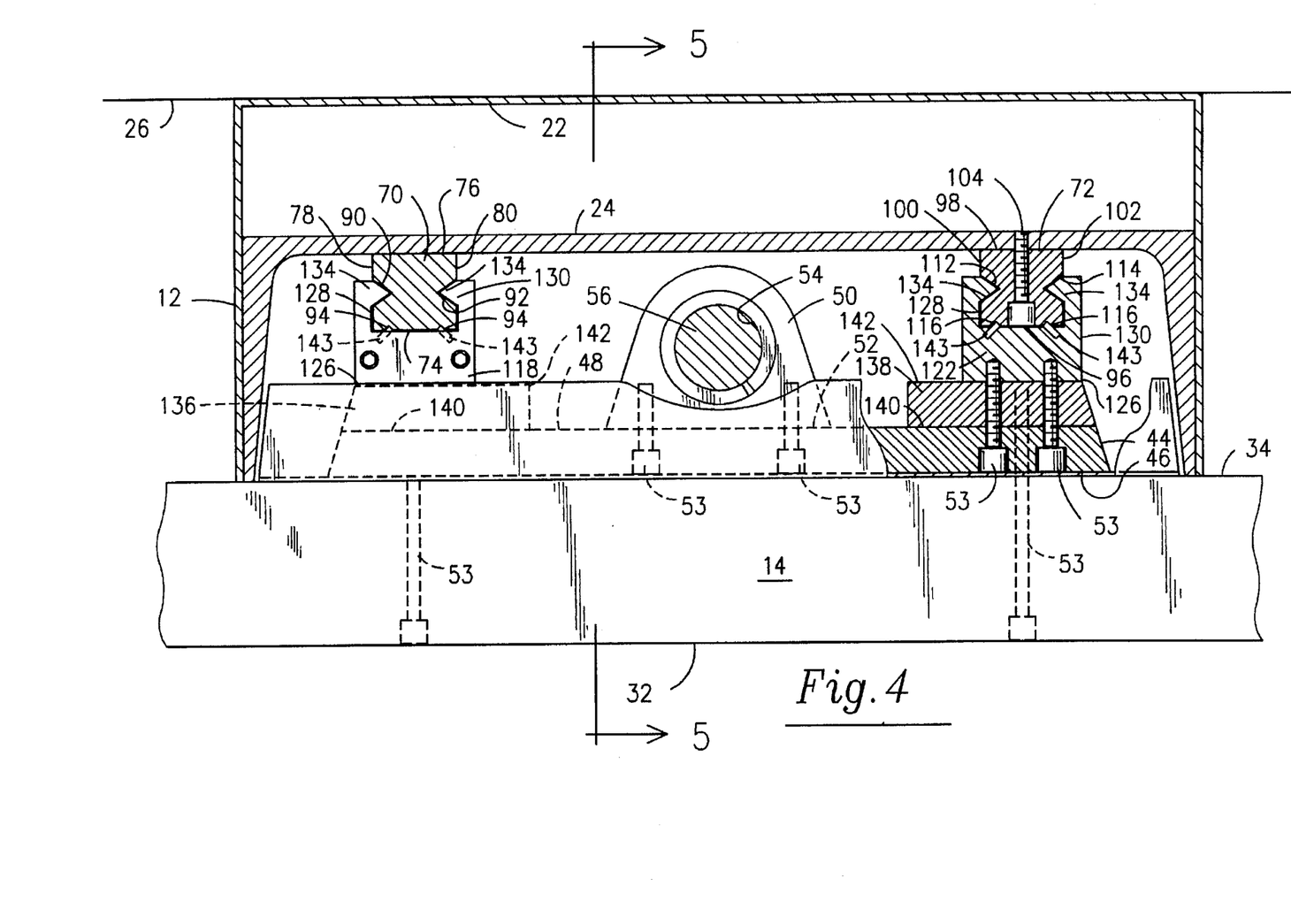
FIG. 4 is a cross-sectional view along lines 4—4 of FIG. 1.
Figure 5:
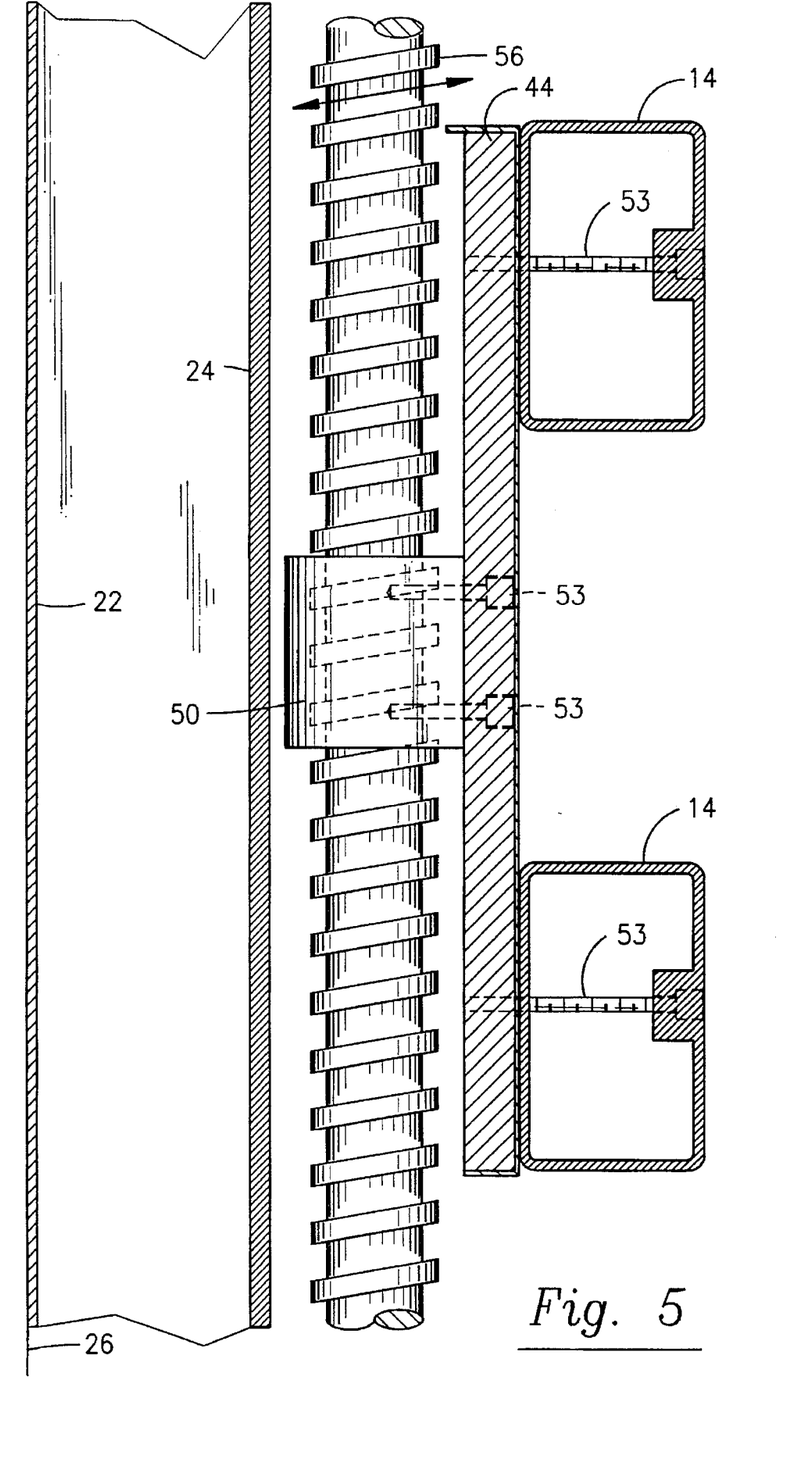
FIG. 5 is a cross-sectional view along lines 5—5 of FIG. 4.

Referring to FIG. 4, a mounting block 44 has opposed front and back surfaces, 46 and 48 respectively. Front surface 46 of mounting block 44 mounts to back surface 34 of c-arm 14 by bolts 53. A screw engagement element 50 has a threaded aperture 54, formed therein, and a front surface 52. Front surface 52 of screw engagement element 50 mounts to back surface 48 of mounting block 44 by bolts 53.

Figure 6:
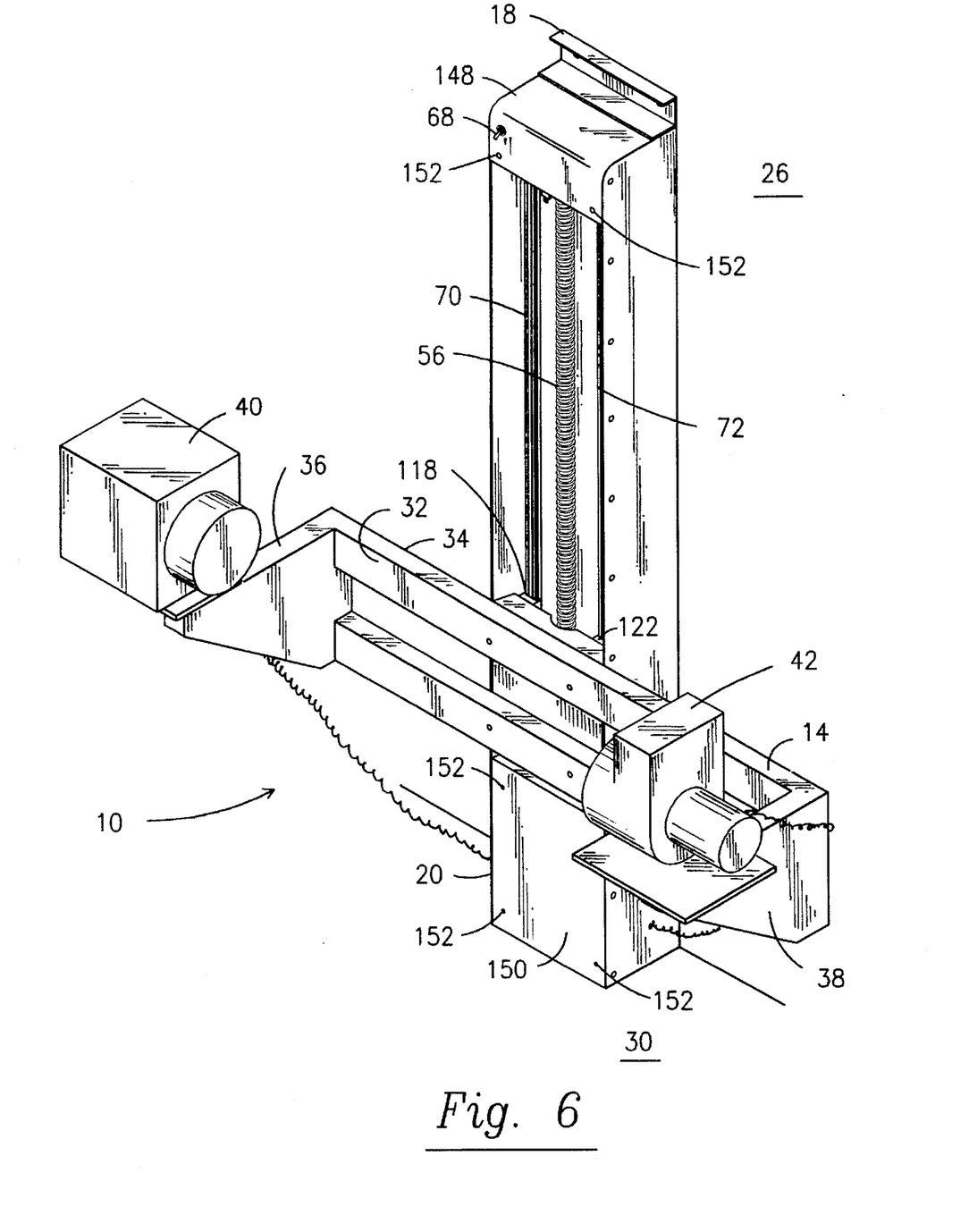
FIG. 6 is a perspective view of the videofluoroscopy device.

Referring to FIG. 1, a worm screw 56 having top and bottom ends, 58 and 60 respectively, is mounted along longitudinal axis 19 in first channel 16 of vertical housing 12. A first bracket 62 is mounted to intermediate wall 24 at top end 18 of vertical housing 12 and engages top end 58 of screw 56. A second bracket 64 integral with intermediate wall 24 at bottom end 20 of vertical housing 12, guides bottom end 60 of screw 56 into a motor 66. Wormscrew 56 intersects threaded aperture 54 of screw engagement element 50. Motor 66 operates in reversible directions causing screw 56 to turn in opposed directions, while communicating with threaded aperture 54 and moving c-arm 14 in opposed vertical directions along longitudinal axis 19 within vertical housing 12. Motor 66 is powered by direct current. As shown in FIG. 2, an electrical plug 67 is provided in bottom end 20 of vertical housing 12 for inserting into a common electrical outlet. A transformer (not shown) is placed along the line of the plug 67 to convert alternating current to direct current thereby powering motor 66. An alternate connection employs a direct current connecting element (not shown) for connection between the motor 66 and a battery source. The motor 66 may also be an alternating current motor, thereby eliminating the need for the transformer or battery. Referring to FIGS. 1 and 6, a three position switch 68 mounted at top end 18 of vertical housing 12 activates motor 66 in reversible directions as well as providing motor 66 with an off state.

Referring to FIG. 1, first and second guide rails, 70 and 72 respectively, are enclosed in first channel 16 of vertical housing 12 parallel to longitudinal axis 19 and paralleling worm screw 56 on opposed sides.

Referring to FIG. 4, first guide 70 has opposed first front and first back surfaces, 74 and 76 respectively, and opposed first left and first right side surfaces, 78 and 80 respectively. First back surface 76 of first guide rail 70 is mounted to intermediate wall 24 of vertical housing 12. Referring to FIG. 1, bolts secure first guide rail 70 to intermediate wall 24 at a first top and first bottom end, 84 and 86 respectively, and a first middle portion 88 of first guide rail 70. Referring to FIG. 4, a first groove 90 is provided along first left side surface 78 and a second groove 92 is provided along first right side surface 80 of first guide rail 70. A pair of first indentations 94 are provided along first front surface 74 of first guide rail 70.

Referring to FIG. 4, second guide 72 has opposed second front and second back surfaces, 96 and 98 respectively, and opposed second left and second right side surfaces, 100 and 102 respectively. Second back surface 98 of second guide rail 72 is mounted to intermediate wall 24 of vertical housing 12. Bolts 104 secure first guide rail 72 to intermediate wall 24 at a second top and second bottom end, 106 and 108 respectively, and a second middle portion 110 of second guide rail 72. Second top end 106, second bottom end 108, and second middle portion 110 of second guide rail 72 is shown in FIG. 1. Referring to FIG. 4, a third groove 112 is provided along second left side surface 100 and a fourth groove 114 is provided along second right side surface 102 of second guide rail 72. A pair of second indentations 116 are provided along second front surface 96 of second guide rail 72.

A first pair of stabilizing elements, 118 shown in FIG. 4, surrounds first guide rail 70, and a second pair of stabilizing elements, 122 shown in FIG. 4, surrounds second guide rail 72. The stabilizing elements are provided to ensure stable longitudinal movement of c-arm 14. Each stabilizing element has a back surface 126, left and right opposed outwardly projecting arms, 128 and 130 respectively, defining a second channel, and opposed inwardly projecting dimples 134. Dimple 134 of left arm 128 of the first pair of stabilizing elements, 118 shown in FIG. 4, communicates with first groove 90 of first guide rail 70. Dimple 134 of right arm 130 of the first pair of stabilizing elements, 118 shown in FIG. 4, communicates with second groove 92 of first guide rail 70. Dimple 134 of left arm 128 of the second pair of stabilizing elements, 122 shown in FIG. 4, communicates with third groove 112 of second guide rail 72. Dimple 134 of right arm 130 of the second pair of stabilizing elements, 122 shown in FIG. 4, communicates with fourth groove 114 of second guide rail 72.

Referring to FIG. 4, first and second spacing members, 136 and 138 respectively, having opposed front and back surfaces, 140 and 142 respectively, are provided. First spacing member 136 is intermediate mounting block 44 and the first pair of stabilizing elements, 118 shown in FIG. 4. Front surface 140 of first spacing member 136 is mounted by bolts 53 to back surface 48 of mounting block 44 and back surface 142 of first spacing member 136 is mounted by bolts 53 to back surface 126 of the first pair stabilizing elements, 118 shown in FIG. 4. Second spacing member 138 is intermediate mounting block 44 and the second pair of stabilizing elements, 122 shown in FIG. 4. Front surface 140 of second spacing member 138 is mounted by bolts 53 to back surface 48 of mounting block 44, and back surface 142 of second spacing member 138 is mounted by bolts 53 to back surface 126 of the second pair of stabilizing elements, 122 shown in FIG. 4. Mounting block 44, first spacing member 136, second spacing member 138, and screw engagement element 50 could be manufactured as one part to be employed in the present invention.

Referring to FIG. 4, a pair of linear bearings 143 are enclosed within each pair of stabilizing elements. Linear bearings 143 are lubricated, cylindrical in shape, and assist in providing fluid movement to c-arm 14. THK linear bearings are employed in the present invention, although other bearings of varying design and manufacture could be employed to achieve the same results. Linear bearings 143 within the first pair of stabilizing elements, 118 shown in FIG. 4, communicate with first indentations 94 of front surface 74 of first guide rail 70. Linear bearings 143 within the second pair of stabilizing elements, 122 shown in FIG. 4, communicate with second indentations 116 of second front surface 96 of second guide rail 72.

Referring to FIG. 1, a first micro limiting switch 144 is mounted to intermediate wall 24 at top end 18 of vertical housing 12. A second micro limiting switch 146 is mounted to intermediate wall 24 at bottom end 20 of vertical housing 12. First and second micro limiting switches 144 and 146, respectively, prohibit c-arm 14 from disengaging from worm screw 56 by stopping the longitudinal movement of c-arm 14 at an upper and lower limit.

Referring to FIG. 6, a top cover 148 is mounted at top end 18 of vertical housing 12 to cover first bracket 62 and top end 58 of worm screw 56. A bottom cover 150 is mounted at bottom end 20 of vertical housing 12 to cover motor 66. Top and bottom cover, 148 and 150 respectively, are mounted by a plurality of bolts 152.

The present invention uses an x-ray device to render an image. The x-ray device emits a high frequency constant potential x-ray beam, although an x-ray device emitting a pulse beam could be used. The x-ray image is transmitted to a video monitor and video tape recorder by a BC type video cable. Any available video tape format could be used with the present invention, including but not limited to Beta, Beta SP, ¾ inch, 8 mm, Hi-8 mm, S-VHS, and VHS. VHS has shown to provide adequate results at the most reasonable cost for the videofluoroscopy device 12.

My invention employs hardened stainless steel for vertical housing 12, c-arm 14, mounting block 44, screw engagement element 50, first and second brackets 62 and 64, first and second guide rails 70 and 72, the stabilizing elements such as 118 and 122, first and second spacing members 136 and 138, top and bottom cover 148 and 150, and all bolts. Any of the above mentioned elements could be manufactured out of a high impact polymer and achieve the desired results.

Equivalent elements can be substituted for the elements employed in this invention to obtain the same results in the same manner.

Having thus described the invention what is claimed and desired to be secured by Letters Patent is:

1. A videofluoroscopy device comprising, a vertical housing enclosing a first channel and having a longitudinal axis, a c-arm supporting an x-ray device and having opposed front and back surfaces, the c-arm mounted perpendicularly to the longitudinal axis, a vertically mounted center screw enclosed within the first channel for moving the c-arm along the longitudinal axis, a mounting block having opposed front and back surfaces and an arcuate portion with a threaded aperture formed therein, the arcuate portion integral with the back surface of the mounting block, the front surface of the mounting block mounted to the back surface of the c-arm, the threaded aperture engaging the center screw, at least two guide rails, each guide rail having opposed side surfaces, opposed front and back surfaces, indentations along the front surface, and a groove along each opposed side surface the guide rails mounted within the first channel parallel to the longitudinal axis, at least two stabilizing elements, each stabilizing element having a back surface, left and right opposed outwardly projecting arms defining a second channel, and opposed inwardly projecting dimples communicating with the groove along one of the opposed side surfaces of the guide rails, the back surface of each stabilizing element mounted to the back surface of the mounting block, the second channel partially enclosing the guide rails, a set of bearings enclosed within each stabilizing element and communicating with the indentations along the front surface of the guide rails, the bearings providing fluid movement to the c-arm, stop means mounted on the vertical housing for limiting the movement of the c-arm, and drive means communicating with the center screw for moving the c-arm along the longitudinal axis.

2. The videofluoroscopy device according to claim 2 wherein the stop means is a pair of micro limiting switches mounted at opposing top and bottom ends of the vertical housing.

3. The videofluoroscopy device according to claim 2 wherein the vertical housing is mounted perpendicular to a floor surface and secured to a wall.

4. The videofluoroscopy device according to claim 2 wherein the x-ray device comprises an x-ray generator and an x-ray image intensifier.

5. The videofluoroscopy device according to claim 4 wherein the x-ray device renders a real time x-ray image to a video monitor and video tape recorder.

6. The videofluoroscopy device according to claim 2 wherein the center screw is a worm screw.

7. The videofluoroscopy device according to claim 2 wherein two guide rails are employed, each guide rail mounted on an opposite side of the center screw.

8. The videofluoroscopy device according to claim 7 wherein a pair of stabilizing elements engage each guide rail.

9. The videofluoroscopy device according to claim 2 wherein a pair of bearings are enclosed within each stabilizing element, each bearing communicating with the guide rail at a tangent point within the indentations along the front surface of guide rail.

10. The videofluoroscopy device according to claim 9 wherein the bearings are linear bearings.

11. A videofluoroscopy device comprising, a vertical housing enclosing a first channel and having a longitudinal axis, the vertical housing mounted perpendicular to a floor surface and secured to a wall, a c-arm having opposed front and back surfaces and opposed first and second ends, the first end supporting an x-ray generator, the second end supporting an x-ray image intensifier, the c-arm mounted perpendicularly to the longitudinal axis, a vertically mounted worm screw enclosed within the first channel for moving the c-arm along the longitudinal axis, a mounting block having opposed front and back surfaces, the front surface of the mounting block mounted to the back surface of the c-arm, a screw engagement element having a threaded aperture and a front surface, the threaded aperture engaging the center screw, the front surface of the screw engagement element mounted to the back surface of the mounting block, two guide rails, each guide rail having opposed side surfaces, opposed front and back surfaces, indentations along the front surface, and a groove along each opposed side surface, each guide rail mounted on an opposite side of the worm screw and paralleling the worm screw within the first channel along the longitudinal axis, two spacing members having front and back surfaces, the front surface of each spacing member mounted to the back surface of the mounting block, two pair of stabilizing elements, each stabilizing element having a back surface, left and right opposed outwardly projecting arms defining a second channel, and opposed inwardly projecting dimples communicating with the groove along one of the opposed side surfaces of the guide rails, the back surface of each stabilizing element mounted to the back surface of the mounting block, the second channel partially enclosing the guide rails, a pair of linear bearings enclosed within each stabilizing element, each linear bearing communicating with the guide rail at a tangent point within the indentations along the front surface of the guide rail, the linear bearings providing fluid movement to the c-arm, a pair of micro limiting switches mounted at opposing top and bottom ends of the vertical housing to prohibit the c-arm from disengaging from the worm screw, and drive means communicating with the worm screw for moving the c-arm along the longitudinal axis.

12. The videofluoroscopy device according to claim 11 wherein the x-ray generator and x-ray intensifier are interchangeable upon the first and second ends of the c-arm.

13. The videofluoroscopy device according to claim 11 wherein the x-ray generator and x-ray image intensifier render a real time x-ray image to a video monitor and video tape recorder.

14. The videofluoroscopy device according to claim 13 wherein VHS format video tape is used in the video tape recorder.

15. The videofluoroscopy device according to claim 11 wherein the drive means is a motor.

16. The videofluoroscopy device according to claim 15 wherein the motor operates in reversible directions.

17. The videofluoroscopy device according to claim 16 wherein the motor is powered by AC current.

18. The videofluoroscopy device according to claim 16 wherein the motor is activated by a switch.

19. The videofluoroscopy device according to claim 16 wherein the motor is powered by DC current.

* * * * *

UNITED STATES PATENT AND TRADEMARK OFFICE
CERTIFICATE OF CORRECTION

PATENT NO. : 5,519,754

DATED : May 21, 1996

INVENTOR(S) : Postlethwaite

It is certified that error appears in the above-identified patent and that said Letters Patent is hereby corrected as shown below:

Column 6, line 1, (claim 2) "claim 2" should read --claim 1--.
Column 6, line 5, (claim 3) "claim 2" should read --claim 1--.
Column 6, line 8, (claim 4) "claim 2" should read --claim 1--.
Column 6, line 13, (claim 6 "claim 2" should read --claim 1--.
Column 6, line 15, (claim 7) "claim 2" should read --claim 1--.
Column 6, line 21, (claim 9) "claim 2" should read --claim 1--.

Signed and Sealed this

Thirtieth Day of July, 1996

Attest:

BRUCE LEHMAN

*Attesting Officer*     *Commissioner of Patents and Trademarks*